(12) United States Patent
Bell et al.

(10) Patent No.: US 9,901,098 B2
(45) Date of Patent: Feb. 27, 2018

(54) METHODS FOR PLANT PROTECTION

(71) Applicant: TDA Research, Inc, Wheat Ridge, CO (US)

(72) Inventors: William Bell, Boulder, CO (US); Christopher Brian France, Arvada, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 53 days.

(21) Appl. No.: 15/255,660

(22) Filed: Sep. 2, 2016

(65) Prior Publication Data

US 2017/0064964 A1 Mar. 9, 2017

Related U.S. Application Data

(60) Provisional application No. 62/214,000, filed on Sep. 3, 2015.

(51) Int. Cl.
*A01N 59/08* (2006.01)
*A01N 59/00* (2006.01)

(52) U.S. Cl.
CPC .................................. *A01N 59/00* (2013.01)

(58) Field of Classification Search
None
See application file for complete search history.

(56) References Cited

U.S. PATENT DOCUMENTS

| | | | | | |
|---|---|---|---|---|---|
| 5,958,463 | A | * | 9/1999 | Milne | A01N 25/28 424/195.17 |
| 2004/0183050 | A1 | * | 9/2004 | Hei | A01N 59/00 252/188.1 |
| 2005/0121308 | A1 | * | 6/2005 | Brownfield | C01B 11/024 204/157.48 |
| 2015/0210964 | A1 | * | 7/2015 | Willey | C11D 3/3953 424/665 |

FOREIGN PATENT DOCUMENTS

TW 201041497 A1 * 12/2010

OTHER PUBLICATIONS

English translation of TW201041497 provided by Google obtained on Feb. 2, 2017.*

* cited by examiner

*Primary Examiner* — Robert T. Crow
*Assistant Examiner* — John P Nguyen
(74) *Attorney, Agent, or Firm* — Brian J. Elliott

(57) ABSTRACT

The present invention relates to a method for treating plant pests or pathogens. The disclosed method of protecting plants against pests includes a plant protection composition, wherein the plant protection composition comprises a water-soluble activator and a benefit active precursor. The composition is applied externally to the plant where a benefit active species is generated in situ, thus mitigating the pest.

15 Claims, 7 Drawing Sheets
(7 of 7 Drawing Sheet(s) Filed in Color)

METHODS FOR PLANT PROTECTION

CROSS-REFERENCE TO RELATED APPLICATIONS

This application claims the benefit of U.S. Provisional Application No. 62/214,000, filed Sep. 3, 2015.

FIELD OF THE INVENTION

The present invention generally relates to methods of protecting plants from pests using a benefit active species produced in situ. The invention further provides materials and methods of protecting plants from pathogens using photochemically generated chlorine dioxide wherein the method generates chlorine dioxide having a concentration in a critical range, wherein the concentration is high enough to treat the pest, and yet low enough that it does not promote unacceptable plant damage or mortality. In addition to protecting growing plants, the present invention also relates to protecting plants in general by treating tools and surfaces used in growing and transporting plants, and to increasing the value of harvested plants and plant products by killing human pathogens present on their surfaces.

BACKGROUND OF THE INVENTION

Strong oxidants, including hydrogen peroxide, peracetic acid, and chlorine dioxide, are effective antimicrobials, including efficacy against bacterial and fungal plant pests. When the pesticide's mode of action is oxidation, for example oxidation of the target organism's cell wall, the target organisms are not likely to develop resistance to the pesticide. Oxidants such as hydrogen peroxide, peracetic acid, and chlorine dioxide readily decompose in the environment to harmless products. A pesticide should preferably have a long residence time; that is, it should remain effective after application to the plant for several days or longer, to minimize the cost and labor of re-application.

There are commercial pesticide products using hydrogen peroxide and peracetic acid. However, their utility is limited by their relatively short residence time on the plant surface. Chlorine dioxide could potentially be an active component in a plant pesticide formulation, however limitations have prevented its use. A solution of chlorine dioxide in water may be generated by combining water solutions of sodium chlorite and an acid or transition metal. The acid may be a mineral acid, such as hydrochloric acid, or an organic (carboxylic) acid, including hydroxycarboxylic acids such as ascorbic acid or citric acid.

One drawback that has prevented the use of chlorine dioxide as a plant pesticide is the fact that it readily decomposes in the environment, limiting the residence time on the plant. In addition, chlorine dioxide is a gas at room temperature; but it is very soluble in water, and is commonly used in water solution. However, when a water solution of chlorine dioxide is sprayed, for example to apply the solution to a plant surface, the chlorine dioxide can disperse (vaporize) into the atmosphere. This is undesirable for two reasons: first, loss of chlorine dioxide decreases the antimicrobial activity; second, chlorine dioxide in the atmosphere produces an inhalation hazard. The permissible exposure level (PEL) for human workers for chlorine dioxide in air is 0.1 ppm. Chlorine dioxide in the atmosphere is hazardous and may require workers to wear Personal Protective Equipment (PPE).

Plants require protection from harmful organisms (pests) including pathogens (that result in plant diseases), bacteria, fungi, viruses, mollusks, worms, arthropods, and arthropod eggs. Existing plant protection products can mitigate the damaging influences of plant diseases and insects using various mechanisms. It is desirable for plant protection products to mitigate a threat, but also to minimize damage to the plant, to minimize the development of resistant microorganisms, to minimize toxicity to humans and other species, and to not harm the environment.

Current practice recognizes the efficacy of activated halogen species as a disinfectant to protect plants against pathogens. For example, Bliss and Bliss (2015; U.S. Pat. No. 9,018,239) describe addition of an anti-pathogen composition based on halogens to irrigation water. Similarly, Yao et al. (2010) show that $ClO_2$ in irrigation water was effective in protecting calla lilies and other flowers against bacteria and fungi.

Yet another attempt at eliminating microorganisms on surface and in biofilms is through the use of a water-insoluble photoactivator to produce chlorine dioxide. Specifically, it is known to use titanium dioxide ($TiO_2$) and a chlorine dioxide precursor in conjunction with exposure to ultraviolet light to generate chlorine dioxide. However, such processes are undesirable due to the use of an insoluble inorganic photoactivator. In addition, titanium dioxide forms particulates which leave undesirable residue. Averett and Averett (2015; U.S. Pat. No. 9,055,751) describe application of a photocatalytic composition comprising zinc-doped titanium dioxide nanoparticles to the surface of plants to treat or prevent plant diseases.

Riggs et al. (2014, U.S. Pat. No. 8,748,347) describe application of materials to plant surfaces to filter out UV light, for the purpose of protecting plants against harmful fungi and bacteria. More specifically, Riggs et al. describe "methods and compositions for controlling, preventing, or treating plant pathogens using UV filters for combating phytotoxin-producing fungi and/or bacteria."

US 2015/0210964, published Jul. 30, 2015, teaches product compositions that include one or more photoactivators to generate one or more benefit active agents, effective as a bleaching agent, stain remover, or antimicrobial and/or in eliminating biofilm. 2015/0210964 also relates to methods for cleaning and/or bleaching surfaces, and for providing a method of disinfecting or sanitizing surfaces and/or removing biofilm. 2015/0210964 is incorporated by reference herein.

To control diseases, growers predominantly use chemical fungicides (Coyier and Roane, 1986; Chase et al., 2005). In 2009, 870 thousand pounds of fungicides (22.4% of the total pesticides) were applied to floriculture and nursery crops (USDA, 2011). Potential adverse impacts of chemicals on the environment and emergence of fungicide-resistant pathogen strains have put pesticides under increased public scrutiny.

These above references contain at least one of the following limitations in regard to protecting plants from harmful organisms: inability to kill or mitigate the harmful organism or its negative effect on the plant, inability to avoid the development of resistant organisms, inability to use non-toxic or environmentally friendly compounds, inability to generate a suitable benefit species within a controlled concentration range for an extended period of time, inability to generate the benefit active species in situ and minimize volatilization, and inability to treat the pest without degrading the commercial value of the plant.

BRIEF SUMMARY OF THE INVENTION

The present invention relates to a method for treating plant pathogens and solves the limitations of the prior art. The invention describes methods to produce a formulation that will be applied to growing plants to protect them against pests. The present invention overcomes the limitations of short residence time and loss of chlorine dioxide to the atmosphere by generating chlorine dioxide on the plant surface (in situ). In one aspect the invention solves the problem of sustaining an effective level of a benefit active species such as chlorine dioxide by providing a photoactivated process to continually generate the chlorine dioxide in situ over an extended period, which may be slower than the spontaneous rate of chlorine dioxide generated by the combination of two reactants. In another aspect, the present invention avoids excess gaseous chlorine dioxide that may have negative effects on a person who is treating plants or crops, and also the present invention provides a more efficient treatment for pests because the benefit active species is generated at the location where it is most needed (on the plant surface).

Accordingly, in another aspect of this invention, chlorine dioxide is generated on the plant surface by applying first a solution of sodium chlorite, and after some interval (minutes to hours or days), applying a second solution containing a reactant that will combine with sodium chlorite to generate chlorine dioxide. The reactant may be a transition metal or a mineral acid, such as hydrochloric acid; more preferably it may be an organic (carboxylic) acid, still more preferably a hydroxycarboxylic acid such as ascorbic acid or citric acid. Alternatively, the user may first apply a solution containing a reactant that will combine with sodium chlorite to generate chlorine dioxide, and then after an appropriate interval apply a solution of sodium chlorite. On the surface the reactants combine to generate chlorine dioxide. This method avoids the loss of chlorine dioxide to the atmosphere during spray or similar application because the chlorine dioxide is generated on the surface after spraying.

The present invention provides a method of protecting plants against pests, the method comprising the steps of: a) providing a plant; b) providing a plant protection composition, wherein the plant protection composition comprises a water-soluble activator and a benefit active precursor; c) applying the plant protection composition externally on the plant; d) generating a benefit active species in situ; and e) mitigating a pest. Optionally, the method also has the embodiment wherein the benefit active species is only generated in situ after applying the plant protection composition externally on the plant. In a further optional embodiment, the method comprising the step of: g) exposing the plant protection composition to light. In this embodiment the water soluble activator is a water soluble organic photoactivator, and the step of generating a benefit active species comprises photogenerating a benefit active species. In a preferred embodiment, the benefit active precursor is sodium chlorite.

In other embodiments, the water soluble organic photoactivator comprises a photoactive moiety selected from the group consisting of erythrosine, eosin, xanthone, xanthene, thioxanthone, thioxanthene, phenothiazine, fluorescein, benzophenone, alloxazine, isoalloxazine, flavin, and mixtures thereof, more preferably erythrosine, riboflavin or eosin. The water soluble organic photoactivator can be activated to a photo-excited state by excitation with incident radiation of a wavelength between about 350 nm and about 750 nm, more preferably between about 400 nm and about 600 nm.

In other embodiments, the water soluble organic photoactivator is present at a concentration of from about 0.1 ppm to about 1,000 ppm, preferably from about 5 ppm to about 100 ppm.

In yet other embodiments, the chlorite salt concentration is from about 0.0001 wt % to about 10 wt %.

Light can be direct sunlight, indirect sunlight or artificial light.

The method comprises treating plants growing either with roots in soil or hydroponically.

In some embodiments, the plant to be protected is a part of the plant that has been detached or harvested.

In an embodiment, the water soluble activator is an organic acid and the benefit active precursor is a chlorite salt. Optionally, the method may further comprise the step of: f) not causing damage to the plant.

In an optional embodiment of the method, the organic acid is ascorbic acid or cysteine.

In yet further embodiments, the step of applying the plant protection composition externally on the plant further comprises the steps of: h) applying the organic acid in a first application step; and i) applying the chlorite salt in a second application step. Alternatively, the step of applying the plant protection composition externally on the plant further comprises the steps of: h) applying the chlorite salt in a first application step; and i) applying the organic acid in a second application step.

In an embodiment, the benefit active precursor and the water-soluble activator are incorporated into a formulation that retains the benefit active precursor and the water-soluble activator on a plant surface, and slows benefit active precursor and water-soluble activator removal by rain or by irrigation water.

It has now been surprisingly found that providing a plant protection product composition according to the present invention enables the generation of one or more benefit active agents at a critical concentration range over an extended period of time such that the concentration is high enough to be effective as a pathogen killing agent, while low enough so that is does not kill or damage the plant. It is surprising that there would be a level of sodium chlorite that could be used to produce chlorine dioxide on a plant surface that would be beneficial to a plant. Prior art shows that levels of sodium chlorite and chlorine dioxide that are used as an antimicrobial surface treatment will damage plant tissue. Thus, prior art teaches that sodium chlorite and chlorine dioxide use on plants would be undesirable.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
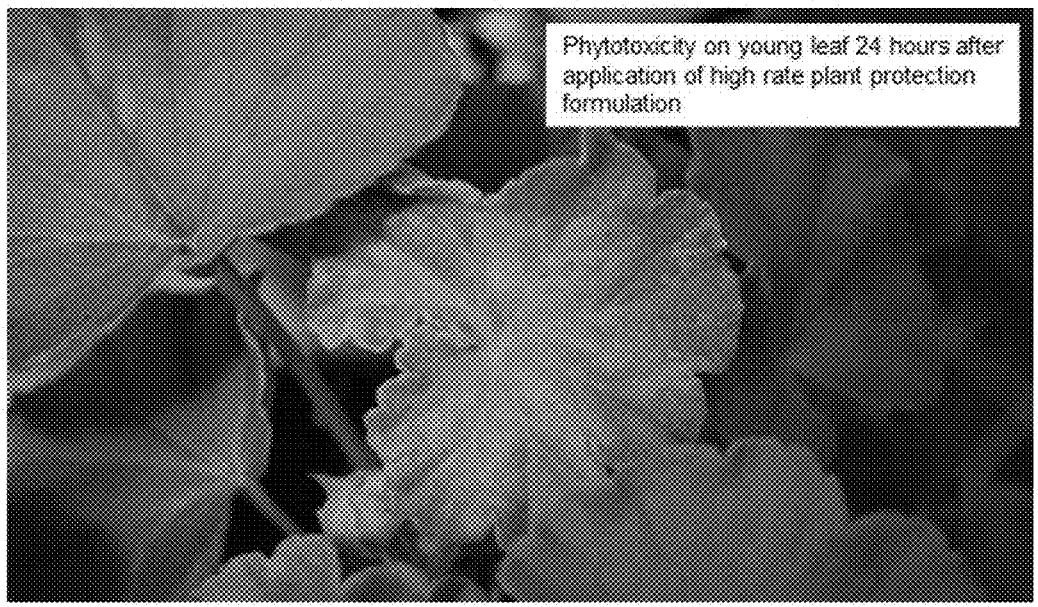
FIG. 1. Phytotoxicity on young leaf 24 hours after application of a high rate of plant protection formulation, as described in Example 1.
Figure 2:
FIG. 2. Non-treatment, non-diseased, Water control, as described in Example 1.
Figure 3:
FIG. 3. Non-treated, disease control, as described in Example 1.
Figure 4:
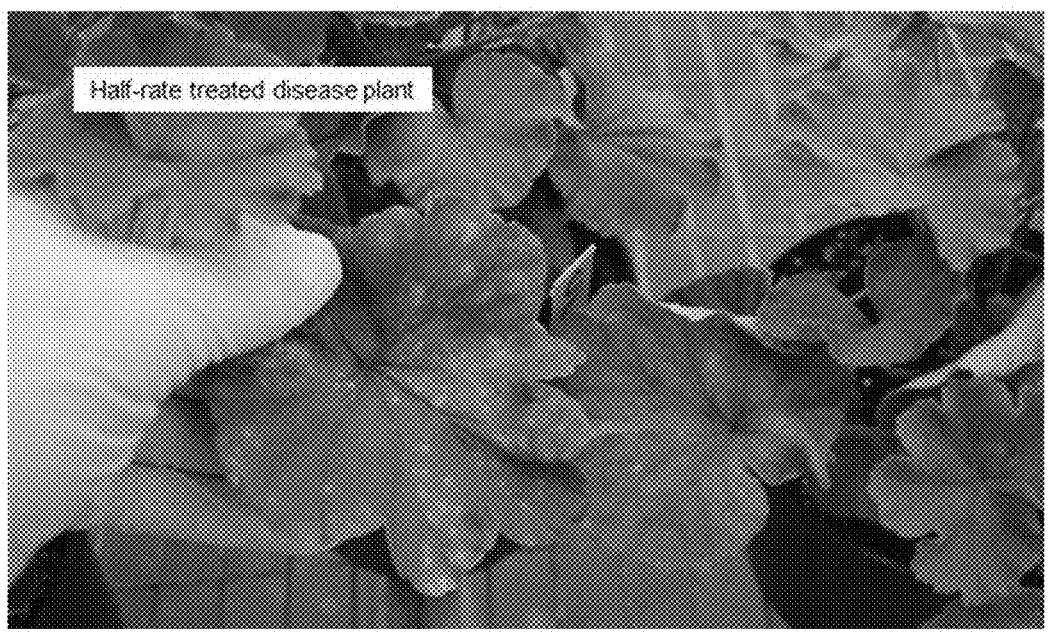
FIG. 4. Half-rate treated disease plant, as described in Example 1.
Figure 5:
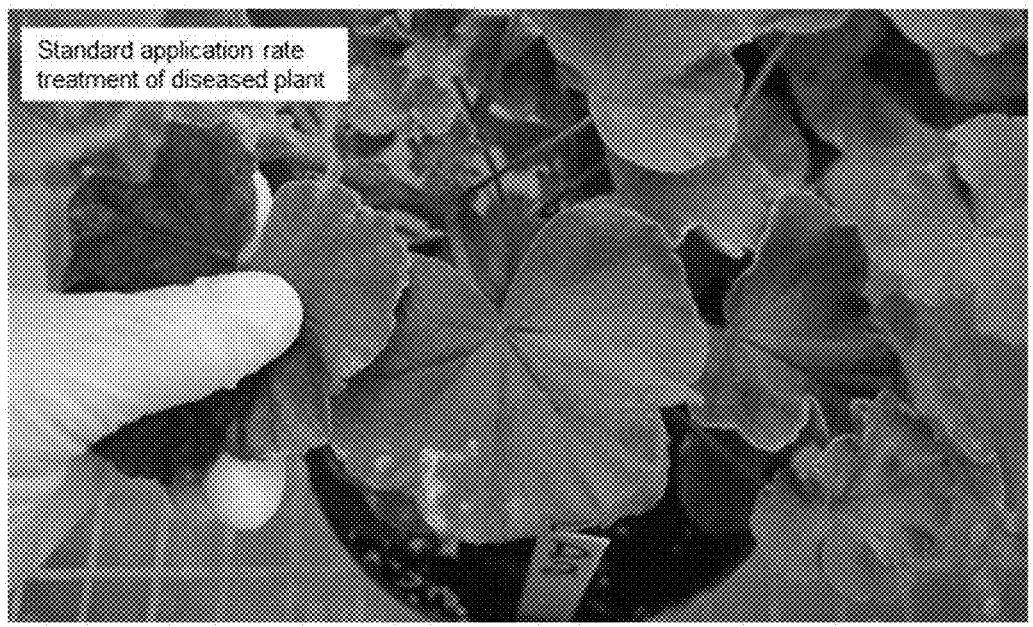
FIG. 5. Standard application rate treated of diseased plant, as described in Example 1.
Figure 6:
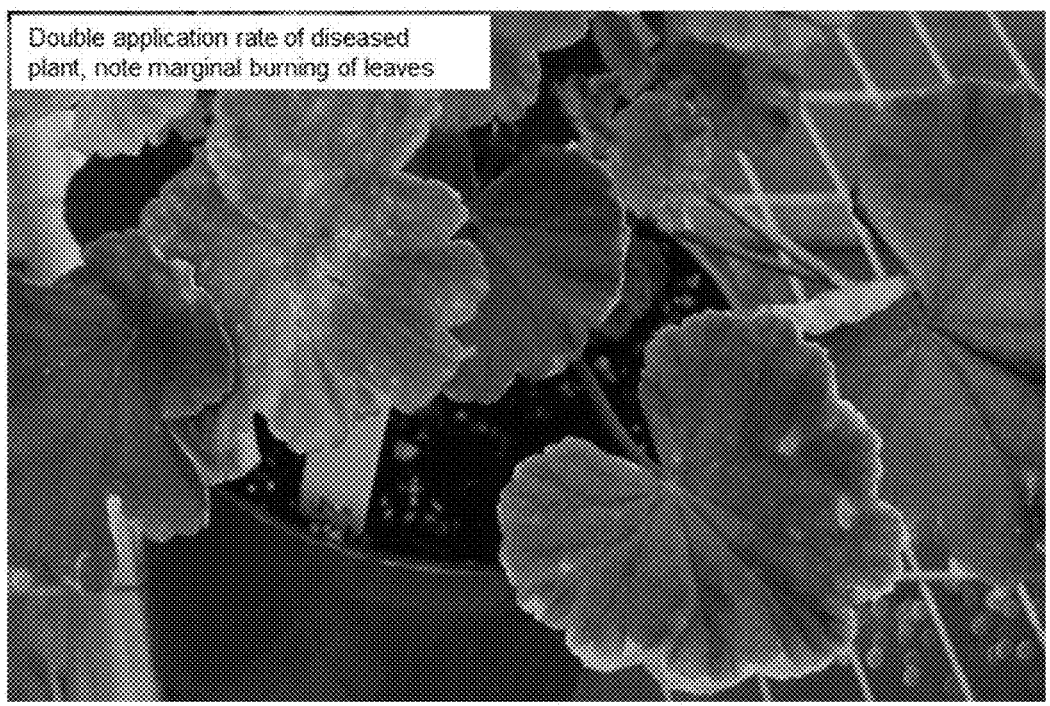
FIG. 6. Double application rate of diseased plant, as described in Example 1—note marginal burning of leaves.

The summary of the invention above and in the Detailed Description of the Invention, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, and article "comprising" (or "which comprises") component A, B, and C can consist of (i.e. contain only) components A, B, and C, or can contain not only components A, B, and C but also one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending on the variable being defined). For example, "at most 4" means 4 or less than 4, and "at most 40%" means 40% or less than 40%. When, in this specification, a range is given as "(a first number) to (a second number)" or "(a first number)-(a second number)", this means a range whose lower limit is the first number and whose upper limit is the second number. For example 25 to 100 mm means a range whose lower limit is 25 mm, and whose upper limit is 100 mm.

The term "raw agricultural commodity" means any food in its raw or natural state, including all fruits that are washed, colored or otherwise treated in their unpeeled natural form prior to marketing). Plant means any of a kingdom (Plantae) of multicellular eukaryotic mostly photosynthetic organisms. Plants usually have leaves or flowers, and need sun and water to survive. Plants may be grown in soil or in water (hydroponically). Plant also means any part of the plant, whether attached or detached (harvested). Plants include ornamental plants including flowers, trees, grasses, food crops, fruits, berries, nuts and vegetables, and cut flowers.

Pests are invertebrate living organisms that cause undesired effects. Non limiting examples include bacteria, fungi, oomycetes, viruses, arthropods, nematodes and mollusks (snails and slugs).

Mitigate a pest means control, eliminate or minimize the negative effects caused by the pest.

Damage to a plant means decreasing the commercial value or appeal of the plant or any part of the plant, whether attached or detached (harvested). Examples of damage to a plant include causing the plant to die or wilt, producing burns or spots on the plant leaf that decrease the plant's commercial value, decreasing the plant's production of commercially valuable items (for example, decreasing the yield of fruit from a fruit tree), or producing harmful materials that cause the plant or plant product to be unfit or less desirable for consumption by humans or animals.

Figure 7:
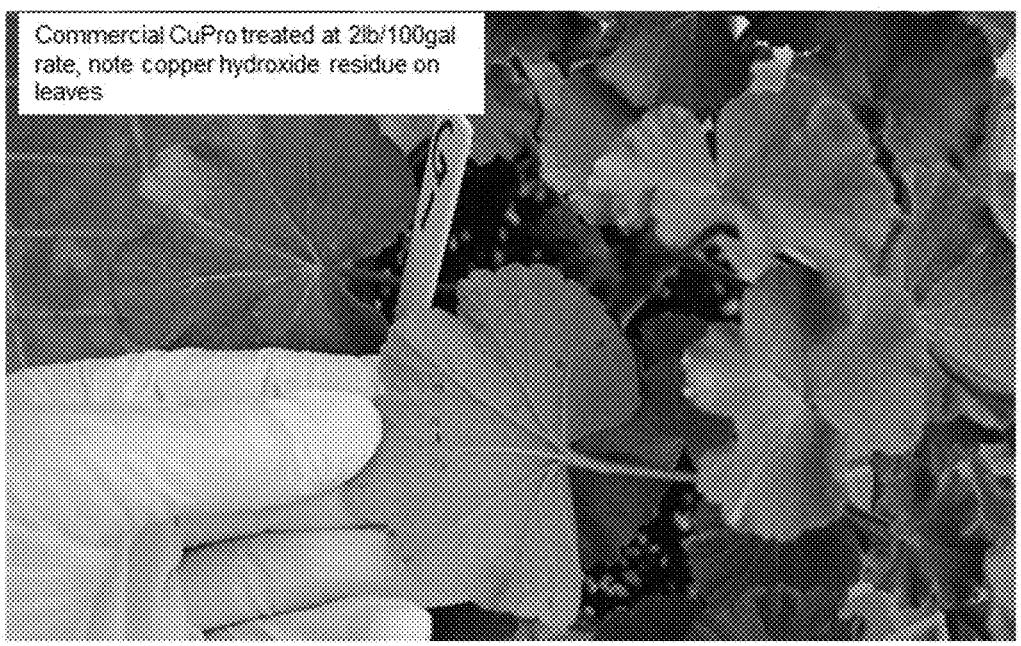
FIG. 7. Commerical CuPro treated at 2 lb/100 gal rate treated plant, as described in Example 1—note copper hydroxide residue on leaves.

Photo-$ClO_2$ and photo-$ClO_2$ technology means a water solution of sodium chlorite and a photoactivator used to photogenerate $ClO_2$ As shown in Example 1, when a solution based on the present invention is applied to leaves of geranium plants, and those leaves are then inoculated with *Xanthomonas* leaf spot disease, the leaves treated with a solution based on the present invention show fewer leaf spots produced by *Xanthomonas* than those of control leaves treated only with water and then inoculated with *Xanthomonas*. Use of the invention has mitigated the *Xanthomonas* pest. Further, as shown in Example 1, when geranium leaves were treated with CuPro, a commercial pesticide in which the active ingredient is copper hydroxide (product of SePRO Corporation, Carmel Ind.)), and then inoculated with *Xanthomonas*, the decrease in leaf spots in the leaves treated with CuPro was comparable to the decrease in leaf spots observed in the leaves treated with a solution based on the present invention. However, CuPro is known to leave residue on the leaves (as shown in FIG. 7), which damages the leaves by decreasing their esthetic appeal and commercial value. The example illustrates how use of the present invention allows one to mitigate a pest while not damaging the plant.

Organic acid means a carboxylic acid having the formula RCOOH, where R is an alkyl or aryl group. More generally, organic acid means an organic compound with acidic properties. The most common organic acids are the carboxylic acids, whose acidity is associated with their carboxyl group —COOH. Other organic acids include sulfonic acids and phenols.

The present invention provides a method of protecting plants against pest wherein a plant is treated with a composition that comprises a water-soluble activator and a benefit active precursor. This composition is applied to the surface of a plant (for example by spraying) and while it is on the plant's surface the water-soluble activator and a benefit active precursor generate a benefit active species. A non-limiting examples of the water-soluble activator is an organic acid such as ascorbic acid. A preferred benefit active precursor is sodium chlorite. A non-limiting example of a benefit active species is chlorine dioxide. The benefit active species of the present invention is produced in situ (on the plant's surface) and this minimizes loss to vaporization. In contrast, if an aqueous solution containing dissolved chlorine dioxide is sprayed, a significant portion of the chlorine dioxide will vaporize (prior to contacting the plant), as it is a gas at room temperature.

In one embodiment of this invention the water soluble activator is a water soluble photoactivator and the process of generating the benefit active species (for example chlorine dioxide) involves the photogeneration of the chlorine dioxide. Non-limiting examples of water soluble organic photoactivators include erythrosine, eosin, xanthone, xanthene, thioxanthone, phenothiazine, fluorescein, benzophenone, alloxazine, flavin and mixtures thereof. In preferred embodiments the organic photoactivator is approved for use on food products, for example erythrosine, riboflavin or eosin.

The photoactivation may occur by exposure to sunlight, filtered sunlight (for example a greenhouse) or artificial light. In preferred embodiments the incident light (electromagnetic radiation) has a wavelength between about 300 nm and about 750 nm, more preferably between about 400 nm and about 600 nm. In certain embodiments, the water soluble organic photoactivator is present at from about 0.1 ppm to about 1,000 ppm, more preferably from 5 ppm to 100 ppm.

The benefit active precursor, which may preferably be a chlorite salt or most preferably sodium chlorite, may be present from about 0.01 wt % to about 1 wt %.

The method of the present invention can be used on plants growing with roots in soil, plants growing hydroponically, or used on parts of plants that have been detached or harvested from the rest of the plant (non-limiting examples include, harvested fruits, grains and vegetables or cut flowers).

The benefit active precursor is preferably sodium chlorite, $NaClO_2$. It may also be another chlorite salt, including but not limited to salts where the cation is lithium, potassium, rubidium, cesium, magnesium, calcium, barium, and ammonium, including alkyl ammonium. The benefit active precursor may also be chlorous acid, $HClO_2$, which is converted to chlorite ion by increasing the pH. Alternatively, the chlorite ion reactant may be produced by any of the processes that are documented for use in producing chlorite from other chlorine-containing species.

Although not wanting to be bound by theory, pathogens cannot readily develop resistance to $ClO_2$ because chlorine dioxide is a strong oxidant. For example, according to the Fungicide Resistance Action Committee (FRAC) classification of the Mode of Action of Fungicides, the photo-$ClO_2$ system would be classified in category M, having multi-site contact activity. Materials in category M are "generally considered as a low risk group without any signs of resistance developing to the fungicides." Specifically, ClO2 would be classified as "Inorganic" along with copper salts (FRAC code M1) and sulfur (code M2).

In one embodiment, the present invention is particularly effective against pathogens that are spread on surfaces, such as windborne spores.

In another embodiment, the method is environmentally friendly; in contrast to many pesticides, its components will not accumulate in the environment or in animal tissue. Although not wishing to be bound by theory, sodium chlorite and chlorine dioxide released into the environment undergo reduction in contact with organic matter, and are ultimately reduced to chloride ion. The photocatalyst may be selected from the broader class of photocatalysts, such that the selected one is benign in the environment. For example: riboflavin (Vitamin B2, found in milk and leafy vegetables) is an effective photocatalyst. Riboflavin is on the FDA Generally Recognized as Safe (GRAS) list. Other examples of environmentally friendly photoactivators include eosin and erythrosine. It may be desirable to have an environmentally friendly formulation that is able to be certified as organic by organizations such as the Organic Materials Review Institute. In one embodiment a water-soluble activator and a benefit active precursor may be selected such that both can be certified as organic. Non-limiting examples of water-soluble activators include citric acid and erythrosine; a non-limiting example of benefit active precursor is sodium chlorite.

In an embodiment, the method is effective against bacterial spores, which are more difficult to destroy than viruses and vegetative organisms.

In a preferred embodiment, the photo-$ClO_2$ system uses a feedstock of aqueous sodium chlorite ($NaClO_2$), a water soluble organic photocatalyst and in optional embodiment also contains a surfactant or agricultural wetting adjuvant to help wet plant surfaces. The solution may be sprayed from an applicator. The sodium chlorite, photocatalyst and surfactant may be pre-packaged as concentrates that are dissolved in water prior to application. Once the solution is prepared it may be sprayed onto the desired foliage and surfaces. In an embodiment, the solution continues to produce effective, low levels of chlorine dioxide under exposure to light, for days (or longer). In one embodiment the solution continues to produce effective, low levels of chlorine dioxide under exposure to light, for about an hour, in another embodiment for about a day, in another embodiment for about a week, in another embodiment for about one month. In another embodiment the plant protection product that was applied from an aqueous solution is allowed to dry out on the surface of the plant, and later it is re-wetted. This re-wetted plant protection product produces effective, low levels of chlorine dioxide under exposure to light. The chlorine dioxide turnover has been shown to continue as long as the surface is wet and light is present. Outdoor photochemical dye bleaching, which demonstrates the oxidative potential of the solution, has shown that the amount of chlorine dioxide that is produced is approximately 300 ppm. It should be understood that this value was measured from a test in the absence of any oxidizable species. As such, if oxidizable species were present it may not be possible to measure a concentration of chlorine dioxide, or the measured chlorine dioxide may be lower than 200 ppm because it is being consumed in situ while it is being generated.

In an embodiment, the light level and spectrum for the method is light in a greenhouse, a typical level is in the range of 900 to 1200 foot-candles (ca. 9,700 to 13,000 lux). For comparison, light levels on an overcast day are about 1,000 lux, and full (but not direct) sun is 10,000 to 25,000 lux. Calculations assuming a 10 nm absorption band (from white light) and a 50% quantum efficiency, confirm that the method will perform suitably at light levels of 1,000 lux or less. In short, if the light level and spectrum are sufficient to grow plants, the method can provide an effective concentration of $ClO_2$ $ClO_2$ effectively kills microbes at concentrations of 1 ppm or less. The time required for $ClO_2$ to kill microbes depends on the concentration, but data show efficacy on various organisms at times as short as one minute with solutions containing 1 ppm $ClO_2$ or less in aqueous solutions.

The surfactants used in the plant protection composition may optionally be commercially available agricultural products designed to be biodegradable. The surfactants may be selected to have the traits: 1) they do not interfere with either the chlorine dioxide oxidant or photo-catalytic generation process, 2) they do not shorten the lifetime of the oxidants nor react with the generated oxidants, 3) they are very effective at wetting surfaces and promote the lifting of microbial contaminants, 4) they are biodegradable.

In one embodiment, the entire optional surfactant used in a plant protection product is 85% biodegradable over a 28 day period, per the shake flask method for Total Organic Carbon (TOC).

The photo-$ClO_2$ technology can be used to remove algae, mold and mildew on materials, including wood, concrete, aluminum siding and plastic decking material. For example, algae may grow on floors of greenhouses and produce a slip and fall hazard. It is desirable to remove the algae to mitigate this hazard. The technology is effective in areas that do not receive direct light The formulation of the present invention may be used to treat raw agricultural commodities: fresh produce that is to be consumed without cooking, to remove surface microorganisms and protect human health. Both aqueous solutions and gas phase $ClO_2$ have been used (for gas phase: Nelson et al. 2015; U.S. Pat. No. 8,920,717). As discussed in the background, these prior methods suffer from volatilization of the chlorine dioxide (or start with the gas phase itself). For example, the produce can be harvested, washed with a formulation of this invention, exposed to light for a period sufficient to mitigate harmful organisms or pathogens, rinsed with fresh water, and then offered for sale and consumption. Alternatively, the formulation could be used by consumers to treat produce before consumption.

In another embodiment the method detoxifies a surrogate for anthrax. Our tests used a commercial suspension of *B. subtilis* spores commonly used as a sterilization verification organism due to its robustness to chemical and thermal sterilization methods. Using an Oriel Sol 1A class ABB solar simulator we achieved a complete kill of 8.32 logs of *B. subtilis*, an approved anthrax simulant, within 12 minutes of exposure to a Photo-$ClO_2$ decontaminant solution. Dark control samples were also tested and population counts performed; the dark sample matched the untreated control, confirming that both chlorite and photo-activation are required.

Tests to establish the efficacy of the photo-$ClO_2$ formulation against anthrax simulants on relevant real world surfaces were also performed. The surfaces that were selected included glass, plastic, painted drywall and sand (Arizona Test Dust). These tests used spores of *B. thuringiensis*, another recognized anthrax surrogate. In all cases we found that the Photo-$ClO_2$ method was capable of sterilizing the surface of these substrates. During this task, *B. thuringiensis* spores were completely killed at a 6 log reduction level on all surfaces within an hour. The only exception was the painted drywall, which required a longer exposure period to completely kill the spores.

In another embodiment the plant protection composition can be applied as a dilute solution in water using standard, commercially available applicators. The $ClO_2$ is produced after the solution leaves the sprayer; this simplifies logistics because one only needs to transport and store a salt/activator mixture (as a solid), not a reactive species.

The photo-$ClO_2$ technology produces chlorine dioxide as long as it is wet and exposed to light of the appropriate wavelength. We have also been able to show that the formulation can be applied and then allowed to completely dry. The solution will reactivate and produce chlorine dioxide with the dried solution is re-wetted and the components presumably re-dissolved. We have shown that the reactivation can happen even after the solution has been dry for 24 hours, 2 days, 5 days or longer. Reactivation can happen from non-porous surfaces such as glass or particulates such as soil as demonstrated on Arizona Test Dust.

In an embodiment, the active ingredients (chlorite, photocatalyst and surfactant package) are easily shipped, even by airborne carriers such as FedEx, UPS, etc. The photo-$ClO_2$ system is safe for the operator as the user never mixes or carries any highly reactive or toxic materials.

Formulations of this invention can use selected components so that the final formulation will be classified as a natural or organic plant protection product or pesticide. Sodium chlorite can be allowed in organic pesticides, as elemental sulfur and copper salts are allowed in organic pesticides. Some photoactivators are natural products and/or on the FDA's Generally Recognized as Safe (GRAS) list. An example natural product photoactivator is riboflavin, 5'-(dihydrogen phosphate), Vitamin B2. Other additives that may be desirable in a plant protection formulation are also available as products consistent with organic classification. For example, Therm X-70 is an Organic Materials Review Institute (OMRI) listed, natural wetting agent and spreader-sticker that is derived from *Yucca*

Photoactivator: The water soluble photoactivators of the present invention may comprise a photoactive moiety and a hydrophilic moiety. An extensive list of potential photoactivators can be found at US 2015/0210964, which is incorporated by reference herein. For purposes of the present invention, the term "hydrophilic moiety" refers to a moiety that is attracted to water and dissolves in water to form a homogenous solution. In one embodiment, the hydrophilic moiety is selected from the group consisting of water soluble oligomers, water soluble polymers and water soluble copolymers. In one preferred embodiment, the hydrophilic moiety may be selected from the group consisting of alkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, polysaccharides, 2-ethyl-2-oxazoline, hydroxyethyl methacrylate, vinyl pyridine-N-oxide, diallyl dimethyl ammonium chloride, maleic acid, lysine, arginine, histidine, aspartic acid, glutamic acid, serine, threonine, asparagine, glutamine, isopropyl acrylamide, styrene sulfonic acid, vinyl methyl ether, vinyl phosphoinic acid, ethylene imine, and mixtures thereof. In one especially preferred embodiment, the hydrophilic moiety may be selected from the group consisting of alkylene oxide oligomer polymers, alkylene oxide oligomer copolymers, vinyl alcohol, vinyl pyrrolidone, acrylic acid, acrylamide, cellulose, and mixtures thereof. For purposes of the present invention, the term "photoactive moiety" refers to an organic conjugated moiety that is capable of absorbing a photon of light and thereby forming an excited state (singlet or triplet). It will be understood that the term "photoactive moiety" does not, however, refer to a charge-transfer excited state. It will further be understood that the photoactive moieties, as disclosed herein, may include a single moiety or a combination of two, three, four or any other number of moieties, as known in the art.

In one embodiment of the present invention, the photoactive moiety is selected from the group consisting of 1,1'-biphenyl-4,4'-diamine, 1,1'-biphenyl-4-amine, benzophenone, 1,1'-biphenyl-4,4'-diol, 1,1'-biphenyl-4-amine, 1,1'-biphenyl-4-ol, 1,1':2', 1"'-terphenyl,1,1':3',1"-terpheny 1,1,1':4',1":4",1"'-quaterphenyl, 1,1':4',1"-terphenyl, 1,10-phenanthroline, 1,1'-biphenyl, 1,2,3,4-dibenzanthracene, 1,2-benzenedicarbonitrile, 1,3-isobenzofurandione, 1,4-naphthoquinone, 1,5-naphthalenediol, 10H-phenothiazine, 10H-phenoxazine, 10-methylacridone, 1-acetonaphthone, 1-chloroanthraquinone, 1-hydroxyanthraquinone, 1-naphthalenecarbonitrile, 1-naphthalenecarboxaldehyde, 1-naphthalenesulfonic acid, 1-naphthalenol, 2(1H)-quinolinone, 2,2'-biquinoline, 2,3-naphthalenediol, 2,6-dichlorobenzaldehyde, 21H,23H-porphine, 2-aminoanthraquinone, 2-benzoylthiophene, 2-chlorobenzaldehyde, 2-chlorothioxanthone, 2-ethylanthraquinone, 2H-1-benzopyran-2-one, 2-methoxythioxanthone, 2-me thy 1-1,4-naphthoquinone, 2-methyl-9 (10-methyl)-acridinone, 2-methylanthraquinone, 2-methylbenzophenone, 2-naphthalenamine, 2-naphthalenecarboxylic acid, 2-naphthalenol, 2-nitro-9(10-methyl)-acridinone, 9(10-ethyl)-acridinone, 3,6-qcridinediamine, 3,9-dibromoperylene, 3,9-dicyanophenanthrene, 3-benzoylcoumarin, 3-methoxy-9-cyanophenanthrene, 3-methoxythioxanthone, 3'-methylacetophenone, 4,4'-dichlorobenzophenone, 4,4'-dimethoxybenzophenone, 4-bromobenzophenone, 4-chlorobenzophenone, 4'-fluoroacetophenone, 4-methoxybenzophenone, 4'-methylacetophenone, 4-methylbenzaldehyde, 4-methylbenzophenone, 4-phenylbenzophenone, 6-methylchromanone, 7-(diethylamino)coumarin, 7H-benz[de]anthracen-7-one, 7H-benzo[c]xanthen-7-one, 7H-furo[3,2-g][I]benzopyran-7-one, 9(10H)-acridinone, 9(10H)anthracenone, 9(10-methyl)acridinone, 9(10-phenyl)-acridinon, 9,10-anthracenedione, 9-acridinamine, 9-cyanophenanthrene, 9-fluorenone, 9H-carbazole, 9H-fluoren-2-amine, 9H-fluorene, 9H-thioxanthen-9-ol, 9Hthioxanthen-9-one, 9H-thioxanthene-2,9-diol, 9H-xanthen-9-one, acetophenone, acridene, acridine, acridone, anthracene, anthraquinone, anthrone, a-tetralone, benz[a]anthracene, benzaldehyde, benzamide, benzo[a]coronene, benzo[a]pyrene, benzo[f]quinoline, benzo[ghi]perylene, benzo[rst]pentaphene, benzophenone, benzoquinone, 2,3,5, 6-tetramethyl, chrysene, coronene, dibenz[a,h]anthracene, dibenzo[b,def]chrysene, dibenzo[c,g]phenanthrene, dibenzo[def, mno]chrysene, dibenzo[def, p]chrysene, DL-tryptophan, fluoranthene, fluoren-9-one, fluorenone, isoquinoline, methoxycoumarin, methylacridone, michler's ketone, naphthacene, naphtho[1,2-g]chrysene, N-methylacridone, p-benzoquinone, p-benzoquinone, 2,3,5,6-tetrachloro, pentacene, phenanthrene, phenanthrenequinone, phenanthridine, phenanthro[3,4-c]phenanthrene, phenazine, phenothiazine, p-methoxyacetophenone, pyranthrene, pyrene, quinoline, quinoxaline, riboflavin 5'-(dihydrogen phosphate), thioxanthone, thymidine, xanthen-9-one, xanthone, derivatives thereof, and mixtures thereof.

Preferably, the photoactive moiety is selected from the group consisting of xanthone, xanthene, thioxanthone, thioxanthene, phenothiazine, fluorescein, benzophenone, alloxazine, isoalloxazine, flavin, derivatives thereof, and mixtures thereof. In one preferred embodiment, the photoactive moiety is thioxanthone.

Other suitable water-soluble photoactivators for the plant protection product compositions of the present invention include fluoresceins and derivatives thereof; preferably halogen substituted fluoresceins; more preferably bromo- and iodo-fluoresceins such as dibromofluorescein, diodofluorescein, rose bengal, erythrosine, eosin (e.g. Eosin Y). In another preferable embodiment the photoactive moiety is erythrosine (red dye #3).

It is still another aspect of the present invention that the photoactive moiety has an absorption band between about 350 nm and about 750 nm, about 350 nm and about 600 nm, about 350 nm and about 420 nm, and about 380 nm and about 400 nm. In another embodiment, the photoactive moiety does not have an absorption band between about 420 nm and about 720 nm, about 500 and about 700 nm, about 500 nm and about 650 nm, and about 500 nm and about 600 nm. In this embodiment, it will be understood that the photoactivator will be substantially colorless to the human eye when used in an aqueous solution at a concentration of about 500 ppm.

In yet another aspect of the present invention, the photoactivator can be activated to a photo-excited state by excitation with incident radiation of a wavelength greater than 350 nm, preferably between about 350 nm and about 750 nm. In one embodiment, the photoactivator can be excited to a "singlet state" and in another a "triplet state", as both of those terms are known in the art.

The photoactivated plant protection product composition may be an aqueous solution, a solid, or incorporated into solution containing other compounds including surfactants.

However, if the photoactivated plant protection product composition is an aqueous composition, the composition may comprise from 1% to 99%, by weight of the composition, of water. It will therefore be understood that the photoactivated plant protection product composition can be in concentrated or diluted form. It is further contemplated that all or a portion of the water may be replaced with another solvent such as ethanol, glycol, glycol-ethers, glycerin, water soluble acetates and alcohols.

In some aspects of the invention exposure to light to induce the formation of the benefit active species is not needed. For example, in an aspect of this invention the water soluble activator is an organic acid and the benefit active precursor is a chlorite salt. The water soluble activator and the benefit active precursor are applied to the plant in separate steps. The order of application is not specific, the water soluble activator or the benefit active precursor may be applied first or second. Once both are on the surface of the plant the benefit active species (for example chlorine dioxide) is produced in situ.

Chlorite ion readily decomposes in the environment, with the final product being chloride ion. Chlorite will undergo oxidation-reduction reactions with components in soils, suspended particles and sediments. Chlorite ion is reduced by bacteria, particularly under anaerobic conditions. Examples of specific compounds that react with chlorite, representative of general classes found in the environment are glucose (carbohydrates), cysteine (amino acids, proteins), and ferrous iron (minerals). Glucose and other aldoses react with chlorite to produce the corresponding carboxylic acid. Cysteine reacts with chlorite to form both cystine and cysteic acid. At neutral pH the disulfide cystine is the primary product. Ferrous iron compounds react with chlorite, producing a precipitate of iron hydroxide.

Methods of Use:

The present invention provides methods of using the compositions of the present invention to provide benefits such as protecting plants and mitigating pests.

As such, in one embodiment the present invention encompasses a method of protecting plants, the method comprising the steps of contacting the surface with a plant protection product composition of the present invention and exposing the plant protection product composition to light, preferably having a wavelength greater than about 350 nm. The light utilized can be from a natural or artificial source.

In another embodiment the present invention further encompasses a method of producing a benefit active agent to kill a pathogen, the method comprising the steps of contacting the pathogen with a plant protection product composition of the present invention and exposing the plant protection product composition to light, preferably having a wavelength greater than about 350 nm.

In another embodiment the present invention further encompasses method of generating a benefit active species on the plant surface by applying first a solution containing a reactant that will combine with sodium chlorite to generate chlorine dioxide, and after some interval (minutes to hours or days), applying a second solution of sodium chlorite. The opposite application can be used as appropriate with similar results.

It is understood that the formulation of this invention may be applied to the plant surface or other surfaces when a pest or pathogen is known to be present, or alternatively applied proactively, before any threat is believed to be present, to mitigate the threat if it becomes present. We have also found that the formulation of this invention can be applied to a plant surface and allowed to dry. If at a later stage the material is re-wetted, the formulation will provide some or all of its original efficacy, and can provide a useful protective effect.

The present invention also relates to a method for treating the surface of a plant using the composition, described in detail above, having at least 0.001 ppm of a photoactivator, described in detail above, followed by exposing the surface of the treated plant to a source of light having a minimal wavelength range of greater than about 300 nanometers up to about 750 nanometers, preferably greater than about 400 nm, up to about 600 nanometers.

Non-limiting examples of synthetic preparation methods for various photoactivators are described in US 2015/0210964, published Jul. 30, 2015, which is incorporated by reference herein.

Plant protection technologies may be used preemptively to prevent diseases from damaging horticulture/crop plants. Use of products in this manner prevents the requirement for diagnosis and treatment once a plant pathogen has already infected and damaged a set of crops.

One embodiment of this invention is its preemptive use by applying the method on a reoccurring frequency to the surfaces of plants. As the plants are re-wetted due to watering or dew condensation, the formulation will become reactivated. This reoccurring production of low levels of chlorine dioxide will keep the plants healthy by killing the plant pathogen that come in contact with the plant while not harming the plant by maintaining a low oxidant concentration.

A typical formulation is 0.05% technical grade sodium chlorite (0.4 g $NaClO_2$ per liter), 10 ppm erythrosine, a photoactivator (0.01 g/L), and the balance water.

It is a surprising result that the concentration of sodium chlorite can be set such that the concentration of sodium chlorite and of generated $ClO_2$ produced in situ will be in a critical range high enough to quickly kill or mitigate pests but yet low enough to not damage plants.

The photoactivator can be selected to absorb light effectively in the wavelength available in a particular situation, for example by measuring the absorption spectrum or consulting a published absorption spectrum for the photoactivator. For example, when plants are exposed to outdoor sunlight, the photoactivator may absorb visible or ultraviolet light. For plants in greenhouses or artificial light, the photoactivator may be selected to effectively absorb the light available. In addition, the photoactivator may be selected to be colored or colorless. A colored photoactivator may be desirable so that the solution being applied in s colored, making it easier to identify areas that have been treated. In other situations, a colorless solution may be desirable because it does not change the appearance of the treated item.

Other materials or adjuvants may optionally be added to the formulation, including surfactants or wetting agents to improve the spreading of the formulation on the plant surface and the contact between the formulation and the target pest. When such additives are used, they can be selected by testing to insure that they do not damage the plant and do not interfere with photogeneration of $ClO_2$. Examples include nonionic organosilicone wetting agents and non-ionic surfactants. TDA has tested two commercial products, CapSil® (CapSil® is a 100% active blend of organo-silicone and non-ionic surfactants that enables solutions to spread over the entire leaf surface evenly and is a product of Aquatrols, Paulsboro, N.J.) and Silwet® (Silwet® L-77 is a silicone surfactant that is a modified trisiloxane that combines a very low molecular weight trisiloxane with a polyether group and is a product of Momentive, Waterford, N.Y.), that are regularly used in application of pesticides to plants, and are known to not damage the plants. We found that they do not interfere with photogeneration of $ClO_2$.

Other additives or adjuvants may be selected to improve performance or ease of application, and optimized through routine testing. For example, in some cases it may be desirable to add a plant nutrient or fertilizer to the spray, so that one spray application both protects against pests and provide nutrients.

The formulations of this invention are water solutions, and may be applied through any conventional spray or other application method. For example, systems to control the aerosol droplet size or provide an electrical charge to spray droplets may be used.

The novelty of one aspect of this invention is the continuous on-the-plant photo-generation of a disinfectant (for example, chlorine dioxide) that mitigates harm from bacteria, fungi and other organisms, without harming the plant. It provides continuous-prolonged plant protection capabilities without damage to the plant.

The novelty of another aspect of this invention is the on-the-plant generation of an oxidant disinfectant (for example, chlorine dioxide) that mitigates harm from bacteria, fungi and other organisms, without harming the plant. The generation of chlorine dioxide on the plant by combining two solutions reduces loss of chlorine dioxide to the environment, improving safety and increasing efficacy.

It is understood that the present invention may be applied to protect plants from pests that are present when the formulation is applied to the plant surface (i.e., as a curative) and also to protect plants from pests that may become present after the formulation is applied to the plant surface (i.e., as a preventive). Tests have shown that a formulation containing sodium chlorite and a photoactivator, with optional adjuvants including wetting agents, provides effective protection to plants when applied to the plant one day or more before the pathogen is introduced (Example 1). It is also recognized that sodium chlorite, due to its solubility in water, may be removed by rain or irrigation water, limiting the duration of effective protection.

In a further embodiment of the present invention, the benefit active precursor and the water-soluble activator may be incorporated into a formulation that retains the precursor and activator on the plant surface, and slows the rate at which the precursor and activator are removed by rain or irrigation water. Below we describe two approaches to increasing the time that the precursor and activator are present on the plant surface, which may be used together or in combination. For the formulations described below, it is desirable to select materials that can be certified as organic by the Organic Materials Review Institute (OMRI).

Polymer formulations incorporating salts (like sodium chlorite) are well known, and include controlled release fertilizers that can be applied to the soil and dispense salts such as potassium nitrate over weeks to months. Polymers that incorporate and slowly release sodium chlorite are described by Wellinghoff in U.S. Pat. No. 5,360,609. As described in the '609 patent, the chlorite can be incorporated into monomeric or polymeric amides (e.g. formamide, isopropylacrylamide-acrylamide mixture) or monomeric or polymeric alcohols. The controlled release formulation can be incorporated into particles such as beads, which can then be applied to the plant surface. If necessary the above beads can be incorporated into a formulation that will increase their adhesion to the plant surface. The polymer formulation can be modified as necessary to adjust the rate at which the sodium chlorite and photoactivator are released, for example, release the components over a few days to a few weeks. (see, for example, Subbarao et al. 2013).

Formulations that increase the viscosity of the liquid formulation, and/or increase its adhesion on the surface: These materials are referred to as thickeners or stickers, and may include polyacrylamides, polyolefins (e.g., polyethylene), polysaccharides, vegetable oils or fatty acids. An example of a suitable material is sodium alginate. Alginate may be desirable for use in a pesticidal formulation because it is available in a form certified as organic by the Organic Materials Review Institute (OMRI). The viscosity of a formulation incorporating sodium chlorite, photoactivator and sodium alginate in water may be modified by the addition of a calcium salt. The appropriate concentrations of alginate and calcium may be readily determined by routine experimentation. For example, we carried out photochemical dye bleaching tests, measuring the time required for dye bleaching using a solution of about 1% sodium chlorite and about 10 ppm of a photoactivator in the presence and absence of sodium alginate. These tests are a convenient means to measure the rate at which the active species is generated. When the amount of sodium alginate was increased from zero to 1%, the time to bleach the dye increased from about one minute to less than two minutes, but by less than a factor of two. At the same time, the viscosity increased significantly, which would increase the time that a solution would reside on a surface after application. These tests confirm that sodium alginate is a viscosity-enhancing additive compatible with the formulations of the present invention.

It is also known that solutions of alginate can be gelled by addition of calcium ion. Out tests showed that mixtures of sodium chlorite, photoactivator and alginate can be converted to a transparent gel by addition of calcium ion. The gel does not flow and is not readily soluble in water, and therefore would be an efficient means to retain the formulation on a surface being treated. We also prepared an alginate gel containing photoactivator, chlorite and a dye that is bleached by $ClO_2$. On exposure to light, the dye was bleached, confirming that the gel is capable of generating the benefit active species. A method to maintain generation of the benefit active species on the plant surface is to apply to the plant surface a water solution containing sodium chlorite, a photoactivator, and alginate in an amount sufficient to thicken the solution but still allow spray application and produce a thin, uniform layer of the solution on the plant surface. In a second step, a solution containing a calcium salt (for example, calcium nitrate, a common component in fertilizers) is applied, converting the solution on the surface to a transparent gel. The gel will remain on the surface for a longer time than the solution. Because the gel is transparent, it will allow light to reach the leaf surface and photosynthetic activity to continue, while also generating chlorine dioxide to mitigate pests.

Example 1

Pesticide Efficacy Trials for Ornamental Plant Diseases. There are many bacterial diseases that cause significant economic losses to the ornamental plant industry. The most common diseases are caused by members of the following three genera: *Erwinia, Pseudomonas*, and *Xanthomonas*. Products containing cupric hydroxide, mancozeb, and streptomycin sulfate are frequently applied to help control bacterial pathogens. Both the cupric hydroxide and mancozeb products leave heavy residues on plant surfaces making their use impractical during final stages of plant production. In addition, heavy use in the industry of streptomycin sulfate has made this product ineffective, due to the development of resistance. In this study we examine the efficacy of Formulation 1 for control of *Xanthomonas* leaf spot on geranium. In Formulation 1 the activator is erythrosine. Formulation 1 also contains a commercial concentrated nonionic surfactant, SSDX-12™ (SSDX-12™ is a concentrated detergent that is certified for use on U.S. military aircraft, and is very effective for general aircraft under MIL-PRF-87937 as a type IV heavy duty water dilutable cleaner. SSDX-12™ is non-hazardous and is pH neutral, non-reactive and non-corrosive. It can be used as a formulation of surfactants and is described in detail in U.S. Pat. No. 9,295,865), to more effectively wet the plant surface with the formulation. CuPro® is a commercial pesticide in which the active ingredient is copper hydroxide.

TABLE 1

Test matrix

| Treatment | Solution used | Interval |
|---|---|---|
| 1. Untreated control | — | — |
| 2. Control diseased (Xanthomonas) | — | — |
| 3. ½ Rate Application | Na chlorite 0.2 g, Activator 0.01g, SSDX-12 2.5 ml + 1000 ml water | — |
| 4. Standard Rate Application | Na chlorite 0.4 g, Activator 0.01g, SSDX-12 5 ml + 1000 ml water | — |
| 5. Double Rate Application | Na chlorite 0.8 g, Activator 0.01g, SSDX-12 10 ml + 1000 ml water | — |
| 6. CuPro | 2 lb/100 gal | 14 day |

Geranium plugs were 'Patriot Bright Red' and were transplanted into 6" pots containing Fafard Potting Mix #2. Plants were initially fertilized with 5 g/pot (Osmocote, 15-9-12 with micronutrients) and were hand watered three times a week. Plants were allowed to establish and grow to approximately 15 cm in high. Experiment was done in a greenhouse house with temperatures maintained between 65-90° F. and light levels between 1000 to 2000 foot candles. Experiment was set-up in randomized block design with 3 blocks per treatment (total 10 plants per treatment, total plants 60). A single Formulation 1 product application was done on 05-20-15 at three different application rates. A bactericide CuPro (copper hydroxide, 2 lbs/100 gal) was applied as a standard control on 05-20-15 and 05-27-15 on a product recommended 7 day application interval (Trt 6). Bactericides were mixed in water following manufacture recommendations, and hand sprayed onto plant foliage till run-off.

For production of bacterial inoculum, a culture of *Xanthomonas hortorum* pv. *pelargonii* (formerly *X. campestris* pv. *Pelargoni*, X575) was grown for 48 h at 28±1° C. on Difco Nutrient Agar (Difco Laboratories, Detroit, Mich.), amended with 5% sucrose. Bacteria were harvested from NA plates, suspended in saline (NaCl, 8.5 g/l) and adjusted spectrophotometrically at $A_{600}$ to $1 \times 10^5$ colony forming units per ml. Leaves and stems were sprayed till run-off with bacterial suspensions and enclosed in clear polyethylene bags for 24 h (05-21-15). Noninoculated plants (sprayed with saline) were used as control. Numbers of lesions were counted on each plant on 06-01-15. Treatments were compared using ANOVA and LSD. Visual comparisons were also done to determine if there was any indication of phytotoxicity.

All rates of Formulation 1 were effective at significantly lowering disease severity. The standard and double rates were comparable to the copper hydroxide control without the residue that lowers crop value. However, the double rate of Formulation 1 produced marginal burning of young leaves within 24 hr of application (note photo). Lower rates of Formulation 1 produced minor amounts of leaf burn over a period of weeks.

TABLE 2

Summary of Average Number of Leaf Sports per Plant.

| Material tested | Average leaf spots per plant |
|---|---|
| Water control | 0 |
| Disease control | 284.9 |
| TDA ½ application rate | 168.2 |
| TDA standard application rate | 80.3 |
| TDA double application rate | 47.6 |
| CuPro 2 lbs/100 gal | 44.7 |

Example 2

Test on August 29 showed that spraying chlorite and acid separately produces less $ClO_2$ in the atmosphere and spraying the pre-mixed acid and chlorite:

Tests were conducted to compare the amount of $ClO_2$ in a closed atmosphere produced by spray application of an aqueous solution containing both sodium chlorite and citric acid, in comparison to application of first the sodium chlorite solution, followed by the citric acid solution. In the comparison, over the first five minutes the amount of chlorine dioxide measured in the atmosphere from the mixed solution was greater than the amount of chlorine dioxide produced by the separate solutions by a factor of five. This example illustrates that separate application of the chlorite and acid solutions will lead to less chlorine dioxide being released to the atmosphere, increasing the safety of personnel applying the solutions

What is claimed is:

1. A method of protecting plants against pests, the method comprising the steps of:

a) providing a plant;

b) providing a plant protection composition, wherein the plant protection composition comprises a water-soluble organic photoactivator activator and a benefit active precursor;

c) applying the plant protection composition on the plants surface, such that the benefit active precursor directly contacts the plant's surface;

d) generating a benefit active species in situ on the plants surface; and e) mitigating a pest.

2. The method of claim 1, wherein the benefit active species in only generated in situ after applying the plant protection composition on the plant's surface.

3. The method of claim 1 further comprising the step of: f) exposing the plant protection composition to light and wherein the water soluble activator is a water soluble organic photoactivator, and wherein the step of generating a benefit active species comprises photogenerating a benefit active species.

4. The method of claim 3, wherein the benefit active precursor is sodium chlorite.

5. The method of claim 4, wherein the water soluble organic photoactivator comprises a photoactive moiety selected from the group consisting of erythrosine, eosin, xanthone, xanthene, thioxanthone, thioxanthene, phenothiazine, fluorescein, benzophenone, alloxazine, isoalloxazine, flavin, and mixtures thereof.

6. The method of claim 5, wherein the water soluble organic photoactivator is erythosine, riboflavin or eosin.

7. The method of claim 3, wherein the water soluble organic photoactivator can be activated to a photo-excited state by excitation with incident radiation of a wavelength between 350 nm and 750 nm.

8. The method of claim 7, wherein the water soluble organic photoactivator can be activated to a photo-excited state by excitation with incident radiation of a wavelength between 400 nm and 600 nm.

9. The method of claim 3, wherein the water soluble organic photoactivator is present at a concentration of from 0.1 ppm to 1,000 ppm.

10. The method of claim 9, wherein the water soluble organic photoactivator is present at a concentration of from 5 ppm to 100 ppm.

11. The method of claim 3, wherein the benefit active precursor comprises chlorite salt present at a concentration of from 0.0001 wt % to 0.08 wt %.

12. The method of claim 3, wherein light is direct sunlight, indirect sunlight or artificial light.

13. The method of claim 3, wherein the plant is growing either with roots in soil or hydroponically.

14. The method of claim 3, wherein the plant to be protected is a part of the plant that has been detached or harvested.

15. The method of claim 1, wherein the benefit active precursor and the water-soluble activator are incorporated into a formulation that retains the benefit active precursor and the water-soluble activator on a plant surface, and slows benefit active precursor and water-soluble activator removal by rain or by irrigation water.

* * * * *